United States Patent [19]

Weinstein et al.

[11] 4,359,462
[45] Nov. 16, 1982

[54] **ANTIBIOTIC 67-121, A NEW POLYENE ANTIFUNGAL ANTIBIOTIC PRODUCED BY *ACTINOPLANES CAERULEUS***

[75] Inventors: Marvin J. Weinstein; Gerald H. Wagman, both of East Brunswick; Joseph A. Marquez, Montclair; Mahesh G. Patel, Verona, all of N.J.

[73] Assignee: Schering Corporation, Kenilworth, N.J.

[21] Appl. No.: 149,617

[22] Filed: May 14, 1980

Related U.S. Application Data

[60] Division of Ser. No. 946,934, Sep. 28, 1978, Pat. No. 4,223,130, Continuation-in-part of Ser. No. 780,207, Mar. 22, 1977, abandoned.

[51] Int. Cl.$^3$ ................... A61K 31/71; A61K 35/00; A61K 31/70
[52] U.S. Cl. ................................... 424/181; 424/119; 424/180
[58] Field of Search .................. 424/181, 119

[56] References Cited

U.S. PATENT DOCUMENTS 3,700,768  10/1972  Kunstmann et al. ............... 424/119

*Primary Examiner*—Jerome D. Goldberg
*Attorney, Agent, or Firm*—Carver C. Joyner; Bruce M. Eisen; Gerald S. Rosen

[57] ABSTRACT

A microorganism of the genus *Actinoplanes* produces a novel complex of polyene antibiotics herein designated collectively Antibiotic 67-121 (and sometimes referred to as the Antibiotic 67-121 complex). The individual components are designated Antibiotic 67-121A, Antibiotic 67-121B, Antibiotic 67-121C and Antibiotic 67-121D. The individual components have ultraviolet spectra characteristic of heptaenes. Further, they are orally active against a variety of strains of *Candida albicans* including many clinical isolates thereof.

6 Claims, No Drawings

ANTIBIOTIC 67-121, A NEW POLYENE ANTIFUNGAL ANTIBIOTIC PRODUCED BY *ACTINOPLANES CAERULEUS*

This application is a divisional of co-pending application Ser. No. 946,934, filed Sept. 28, 1978 (now U.S. Pat. No. 4,223,130) which in turn was a continuation-in-part of application Ser. No. 780,207 filed Mar. 22, 1977 (now abandoned).

This invention relates to novel antibiotically active substances, to their preparation and to pharmaceutical compositions containing such substances. More specifically this invention relates to a novel polyene antibiotic complex and the component antibiotics thereof obtainable by cultivation of a hitherto undescribed microorganism of the genus Actinoplanes of the family Actinoplanceae.

A general discussion of macrolide antibiotics is to be found in Kirk-Othmer, Encyclopedia of Chemical Technology, 2nd Edition, Volume 12, pp. 632 et seq. As specified therein, antibiotics having the common feature of a macrocyclic lactone ring are commonly classified as a distinct group of antibiotics, generally termed the macrolide antibiotics. In addition to the lactone ring, the macrolide group of antibiotics are further distinguished by having various ketonic and hydroxyl functions and glycosidically bound deoxy sugars. One sub-grouping is that designated the antibacterial antibiotics. A further sub-grouping, typified by antifungal activity, is that designated the polyene macrolide antibiotics, or more briefly the polyene antibiotics, this sub-grouping being distinguished by having a conjugated double system of from 3 to 7 conjugated bonds. Identification of an antibiotic as a polyene antiboitic is facilitated by the characteristic ultraviolet absorption spectrum. As representative polyene antibiotics there may be mentioned amphotericin A amphotericin B, candicidin, nystatin, perimycin, pimaricin and trichomycin. A general description of polyene antibiotics is to be found in Kirk-Othmer, Encyclopedia of Chemical Technology, 2nd Edition, Volume 16, pp. 133 et seq., while data on the ultraviolet absorption maxima for the above named, and other, polyene antibiotics is given in Umezawa, H. et al., Index of Antibiotics from Actinomycetes, University of Tokyo Press, 1967, pp. 879-885.

In one of its aspects, the present invention provides a novel polyene antibiotic complex designated the antibiotic 67-121 complex, and the component antibiotics thereof herein designated antibiotic 67-121A, 67-121B, 67-121C and 67-121D. These antibiotics have been found to exhibit useful antifungal activity and in specific tests against a variety of strains of *Candida albicans* to possess enhanced antifungal activity as compared with the known polyene antibiotic candicidin. The novel antibiotic 67-121 complex and its component antibiotics are obtainable by cultivation of a hitherto undescribed micro-organism of the genus Actinoplanes.

In another of its aspects, the present invention provides a process for the preparation of an antibiotic complex designated the antibiotic 67-121 complex, or an antibiotic component thereof designated 67-121A, 67-121B, 67-121C and 67-121D, which process comprises cultivating an Antibiotic 67-121 complex—or component—producing microorganism of the genus Actinoplanes in a nutrient medium under aerobic conditions until substantial antibiotic activity is imparted to the medium. Specifically, we have employed a microorganism of a new species designated herein *Actinoplanes caeruleus*.

The Micro-Organism

The specific microorganism employed herein was isolated from a soil sample from a sage brush area in Bristol Cone Park, Calif., and was identified as a member of the family Actinoplanaceae, genus Actinoplanes, and more specifically as a member of a new species designated *Actinoplanes caeruleus*. A representative culture of the microorganism designed *Actinoplanes caeruleus* has been deposited and is now a part of the permanent collection of the Northern Utilization Research and Development Division, United States Department of Agriculture, Peoria, Ill. U.S.A., where it has been assigned accession number NRRL 5325. Sub-cultures of *Actinoplanes caeruleus* NRRL 5325 are available upon request to the aforementioned agency. In addition to the strain of *Actinoplanes caeruleus* deposited, this invention embraces mutants and variants thereof that exhibit the same or substantially the same taxonomical and physiological properties of the deposited strain which properties include the production of Antibiotic 67-121 complex.

The microorganism employed herein was classifiable as being of the genus Actinoplanes on the basis of it producing no aerial mycelium and forming globose to digitate sporangia which upon dehiscence release globose motile spores having a tuft of polar flagella. The micro-organism exhibited characteristics sufficiently different from known species of Actinoplanes, as hereinafter shown, to warrant designation as a new species. The species was designated *Actinoplanes caeruleus* on the basis of the formation of deep blue to blue-green colonies when grown on a variety of media. A surprising, advantageous and distinguishing feature of *Actinoplanes caeruleus* is the ability to produce the novel polyene antibiotic complex, and component antibiotics, herein designated 67-121.

*Actinoplanes caeruleus* is aerobic and grows well on a variety of nutrient media at from 26° to 37° C. At 45° C. and above substantially no growth is observed. Preferably, in the production of antibiotic, cultivation is effected under submerged aerobic conditions at a pH of from 6.5 to 8.0. *Actinoplanes caeruleus* is sensitive to sodium chloride, growing very poorly in media containing 1.5% sodium chloride. It reduces nitrate to nitrite, partially liquifies gelatin, very slowly decomposes cellulose and only slightly hydrolyses starch.

Other taxanomical data for *Actinoplanes caeruleus* are set forth in Tables I–VI as follows:

Table I—Colony characteristics on various media
Table II—Carbohydrate utilisation
Table III—Nitrogen utilisation
Table IV—Comparison of growth characteristics of *A. caeruleus* with other Actinoplanes species
Table V—Comparison of physiological characteristics of *A. caeruleus* with other Actinoplanes species
Table VI—Comparison of carbohydrate utilisation of *A. caeruleus* with other Actinoplanes species.

In Tables I and III the color descriptions given consist of two designations. The first color designation is a color name taken from the "Descriptive Color Name Dictionary", by Taylor, Knoche and Granville, published by the Container Coporation of America, 1950 (U.S.A.), in combination with a color chip number corresponding to the color name, the chip number being taken from the "Color Harmony Manual", 4th Edition, 1958, published by the Container Corporation of America, U.S.A. The second color designation is a synonym or near synonym of the first designation and is taken from the National Bureau of Standards, Circular 553, November 1955 (U.S.A.).

In Table II the medium employed consisted of 1% of the specified carbohydrate, 0,5% yeast extract, 1.5% agar and the remainder water, while in Table III the medium employed consisted of the stated amount of the nitrogen source, 1% glucose, 1.5% agar and the remainder water. Information for Actinoplanes species, other than *Actinoplanes caeruleus*, given in comparative Tables IV to VI was obtained from the following sources:

(e) for *A. philippinensis, A. brasiliensis, A. missouriensis, A. utahensis* from Thieman J. E. et.al., Journal of Antibiotics 22 (1969) pp 119-125, (b) for *A. sp* NRRL 3884 from DOS 2,252,937, and (c) for *A. italacus* from Beretta G., International Journal Systematic Bacteriology 23 (1973) pp 37-42.

TABLE I

Colony Observations on Various Media

| Medium | Observations |
|---|---|
| Glucose Asparagine Agar | Growth: good, plicate, no aerial mycelium, no diffusible pigment |
| | Color: g4lc dusty orange, moderate orange 53 |
| NZ Amine* Glucose Agar | Growth: good, plicate, no aerial mycelium, no diffusible pigment |
| | Color: g5pa bright orange, vivid orange 48 |
| Milk | Growth: good, no aerial mycelium, no diffusible pigment, no hydrolysis (or in some cultures hydrolysis only beneath colonies) |
| | Color: g4na bright orange, vivid orange 48 plicate |
| Bennett's Agar | Growth: good, plicate, no aerial mycelium, no diffusible pigment |
| | Color: g3ne topaz, strong yellowish brown 74 and some darker mottled areas of a dark greenish black |
| Emerson's Agar | Growth: good, plicate, no aerial mycelium, no diffusible pigment |
| | Color: g3ne topaz, strong yellowish brown 74 |
| Tomato Paste Oatmeal Agar | Growth: Fair to good, folded, no aerial mycelium, no diffusible pigment |
| | Color: mixture of g3ea light melon yellow, pale orange yellow 73 and g13½ le med.blue, moderate blue 182 |
| Glucose Yeast Extract Agar | Growth: good, plicate, no aerial mycelium, no diffusible pigment |
| | Color: g3ne amber, deep orange yellow 69 |
| Potato Slice | Growth: good in the presence of CaCO$_3$ fair in the absence of CaCO$_3$ |
| Sucrose Nitrate Agar (Czapek's Agar) | Growth: fair to poor, granular, no aerial mycelium, no diffusible pigment |
| | Color: g4la orange, strong orange 50 |

TABLE I-continued

Colony Observations on Various Media

| Medium | Observations |
|---|---|
| Tyrosine Agar | |
| (a) Tyrosine Yeast extract | Growth: good, crystals poorly dissolved, no diffusible pigment |
| (b) Tyrosine beef extract | Growth: fair, crystals poorly dissolved, faint brown diffusible pigment produced |
| Observations at 2, 7 & 14 days (after Gordon & Smith J. Bact. 69, 147) | |
| Peptone Iron Agar Observations at 2, 7 & 14 days | Growth: fair to poor, no reaction |
| Bromo cresol purple milk | Milk not peptonized, pH unchanged |

*NZ Amine - a peptone resulting from the enzymatic digestion of casein and serving as a source of nitrogen

TABLE II

Carbohydrate Utilization

| Carbohydrate | Observation |
|---|---|
| L-Arabinose | poor growth |
| Cellulose | poor growth |
| D-Glucose | good growth |
| D-Galactose | good growth |
| β-Lactose | fair growth |
| D-Levulose | good growth |
| D-Mannose | good growth |
| D-Raffinose | poor growth |
| L-Rhamnose | good growth |
| Starch | fair growth |
| Sucrose | good growth |
| D-Xylose | poor growth |
| Inositol | good growth |
| D-Mannitol | good growth |
| Sorbitol | poor growth |
| Control 0.5% yeast extract | poor growth |

TABLE III

Nitrogen Utilization

| Nitrogen Source | Observation |
|---|---|
| 0.5% Yeast Extract (Difco*) | Growth: good, raised, folded, no aerial mycelium, no diffusible pigment |
| | Color: g31c amber, deep orange yellow 69 |
| 1.0% NZ Amine** Type A | Growth: good, no aerial mycelium, dark brown diffusible pigment sometimes produced |
| | Color: g4pe orange rust, deep orange 51 |
| 1% Asparagine | Growth: poor, flat, no aerial mycelium, no diffusible pigment |
| | Color: g18pn dark teal blue, dark greenish blue 174 |
| 1% Glutamic Acid | Growth: poor, flat, no aerial mycelium, no diffusible pigment |
| | Color: g18pn dark teal blue, dark greenish blue 174 |
| 1% Sodium Nitrate | Growth: very poor, not recordable |
| 1% Ammonium Nitrate | Growth: very poor, not recordable |

*"Difco" is a registered trade mark (Difco Laboratories Inc., Detroit, Michigan, U.S.A.)
**NZ Amine - a peptone resulting from the anzymatic digestion of casein and serving as a source of nitrogen

TABLE IV

Growth Characteristics of Actinoplanes Species

| Medium | A.caeruleus NRRL 5325 | A.philippinensis ATCC 12427 | A.brasiliensis ATCC 25844 | A.missouriensis CBS 188.64 | A.utahensis CBS 367.66 | Actinoplanes sp. NRRL 3884 | A.italacus ATCC 27366 |
|---|---|---|---|---|---|---|---|
| Bennett's | | | | | | | |

TABLE IV-continued

Growth Characteristics of Actinoplanes Species

| Medium | | A.caeruleus NRRL 5325 | A.philippinensis ATCC 12427 | A.brasiliensis ATCC 25844 | A.missouriensis CBS 188.64 | A.utahensis CBS 367.66 | Actinoplanes sp. NRRL 3884 | A.italacus ATCC 27366 |
|---|---|---|---|---|---|---|---|---|
| Agar | G | good | good | heavy | heavy | good | good | abundant |
| | S | plicate | slightly wrinkled | thick and wrinkled | smooth | wrinkled and glistening | N.D. | wrinkled |
| | C | strong yellow brown, areas of dark greenish black | yellow ochre | deep orange | pale orange | orange | orange | light brown |
| Glucose Asparagine | | | | | | | | |
| Agar | G | good | good | good | good | good | abundant | scarce |
| | S | plicate | smooth | thin and smooth | smooth | smooth and glistening | N.D. | |
| | C | moderate orange | orange | pale rose | deep orange | deep orange | pale orange | light cherry |
| Czapek-Dex | | | | | | | | |
| Agar | G | fair to poor | good | moderate | moderate | moderate | abundant | N.D. |
| | S | granular | slightly wrinkled | thin, wrinkled | smooth | smooth | N.D. | |
| | C | strong orange | yellow ochre | deep orange | straw | straw | medium orange | |
| Nutrient | | | | | | | | |
| Agar | G | fair | moderate | moderate | good | good | scant | abundant |
| | S | granular | smooth and thin | thin and smooth | thick and wrinkled | smooth | | smooth |
| | C | deep orange yellow speckled with dark greenish blue | pale orange | pale orange rose | deep orange | orange | pale orange | deep |
| Potato | | | | | | | | |
| Agar | G | fair to moderate | moderate | good | moderate | moderate | N.D. | abundant |
| | S | flat, membranous | smooth | smooth | thin and wrinkled | smooth and thin | | smooth |
| | C | deep orange yellow | yellow brown | rose orange | pale orange | pale orange | | light with edge |
| Calcium | | | | | | | | |
| Maleate | G | very poor | moderate | good | moderate | moderate | very weak | scarce |
| | S | non-characterisable | smooth | smooth | thin and wrinkled | smooth and thin | | |
| | C | non-characterisable | yellow brown | rose orange | pale orange | pale orange | | pale |

KEY:
G = Growth
S = Surface characteristics
C = Colony color

TABLE V

Physiological Characteristics

| Test | A.caeruleus NRRL 5325 | A.philippinensis ATCC 12427 | A.brasiliensis ATCC 25844 | A.missouriensis CBS 188.64 |
|---|---|---|---|---|
| Starch Hydrolysis | ++ | +++ | +++ | + |
| H$_2$S Formation | − | +/− | − | − |
| melanin | + | − | − | − |
| Tyrosine Hydrolysis | + | + | − | +++ |
| Xanthine Hydrolysis | N.D. | − | − | − |
| Casein Hydrolysis | + | + | + | + |
| Calcium Maleate Hydrolysis | − | + | + | +/− |
| Nitrate Reduction | + | + | + | + |
| Litmus Milk | N.C. N.P. | N.C. N.P. | N.C. N.P. | N.C. N.P. |
| Gelatin Liquification | + | + | + | − |

| Test | A.caeruleus NRRL 5325 | A.utahensis CBS 367.66 | Actinoplanes sp. NRRL 3884 | A.italacus ATCC 27366 | A.armeniacus ATCC 15676 |
|---|---|---|---|---|---|
| Starch Hydrolysis | ++ | + | N.D. | +/− | ++ |
| H$_2$S Formation | − | + | N.D. | + | + |
| Melanin | + | + | + | + | + |

TABLE V-continued

| Physiological Characteristics | | | | | |
|---|---|---|---|---|---|
| Tyrosine Hydrolysis | + | +/− | N.D. | + | ++ |
| Xanthine Hydrolysis | N.D. | − | N.D. | N.D. | N.D. |
| Casein Hydrolysis | + | + | N.D. | + | +++ |
| Calcium Maleate Hydrolysis | − | + | N.D. | − | +/− |
| Nitrate Reduction | + | + | + | +/− | + |
| Litmus Milk | N.C. N.P. | N.C. N.P. | N.C. N.P. | N.C. Peptonised | N.C. Peptonised |
| Gelatin Liquification | + | +/− | + | + | + |

KEY:
− = negative response
+/ = doubtful response
+ = weak positive response
++ = positive response
+++ = strong positive response
N.D. = not determined
N.C. = no coagulation
N.P. = no peptonization

TABLE VI

Comparison of carbohydrate utilization of A.caeruleus with other Actinoplanes species

| Carbohydrate | A.caeruleus NRRL 5325 | A.philippinensis ATCC 12427 | A.brasiliensis ATCC 25844 | A.missouriensis CBS 188.64 |
|---|---|---|---|---|
| Inositol | ++ | ++ | + | − |
| Fructose | ++ | ++ | ++ | ++ |
| Rhamnose | ++ | ++ | ++ | ++ |
| Mannitol | ++ | ++ | ++ | ++ |
| Xylose | − | ++ | ++ | ++ |
| Raffinose | − | ++ | − | − |
| Arabinose | − | ++ | ++ | ++ |
| Cellulose | +/− | + | + | − |
| Sucrose | ++ | ++ | ++ | ++ |
| Glucose | ++ | ++ | ++ | ++ |
| Control | − | − | − | − |

| Carbohydrate | A.caeruleus NRRL 5325 | A.utahensis CBS 367.66 | A.Actinoplanes sp. NRRL 3884 | A.italacus ATCC 27366 | A.armeniacus ATCC 15676 |
|---|---|---|---|---|---|
| Inositol | ++ | − | − | ++ | +/− |
| Fructose | ++ | ++ | ++ | ++ | ++ |
| Rhamnose | ++ | ++ | +/− | ++ | ++ |
| Mannitol | ++ | ++ | ++ | ++ | ++ |
| Xylose | − | ++ | ++ | ++ | ++ |
| Raffinose | − | − | − | − | − |
| Arabinose | − | ++ | ++ | ++ | ++ |
| Cellulose | +/− | − | − | − | N.D. |
| Sucrose | ++ | ++ | +/− | ++ | − |
| Glucose | ++ | ++ | ++ | ++ | ++ |
| Control | − | − | N.D. | − | − |

Key
− = no utilization
+/− = slightly better than control
+ = fair to moderate utilization
++ = strong utilization
N.D. = not determined

Fermentation of the Microorganism

Fermentation, or cultivation, of the microorganism is usually effected in two stages, the first being an inoculum production stage and the second the antibiotic production stage.

Production of the inoculum is typically effected by cultivation in a suitable nutrient medium of a culture from an agar slant of *Actinoplanes caeruleus*.

Antibiotic production is typically effected by cultivation of a sample of the inoculum in a suitable aqueous nutrient medium under submerged aerobic conditions at a temperature of about 23° to 40° C., preferably at 28° C., and at a pH of from about 6.5 to 8.0, with agitation, until substantial antibiotic activity is imparted to the medium. A fermentation time of from about 3 to 7 days may suitably be employed. To determine when peak antibiotic production has been reached, samples of the medium may be periodically assayed for antibiotic content as hereinafter described. In this manner we have found in specific instances that a preferred cultivation period is about 4 days.

As nutrient medium there may be employed any suitable medium containing a source of carbon, for example an assimilable carbohydrate, and a source of nitrogen, for example an assimilable nitrogenous or proteinaceous material.

Preferred carbon sources include glucose, brown sugar, sucrose glycerol, starch, corn starch, lactose, dextrin, molasses, while preferred nitrogen sources include corn steep liquor, autolyzed brewer's yeast, soyabean meal, cottonseed meal, cornmeal, milk solids, pancreatic digest of casein, distiller's solids, animal peptone liquors, meat and bone scraps and the like. Combinations of these carbon and nitrogen sources can be advantageously used. Trace metals, for example, zinc, magnesium, manganese, cobalt, iron, and the like, need not usually be added to the fermentation media since tap water and the unpurified ingredients used as media components generally contains such metals.

Where only small amounts of antibiotic are required then in place of submerged cultivation, surface cultivation may be employed.

In a method employed herein for determining when peak antibiotic production has occurred, a sample of a specified volume of the fermentation medium is taken, the antibiotic extracted therefrom and then assayed using a standard cylinder cup assay method. Extraction of the antibiotic from the sample may be effected using a water-immiscible organic solvent such as chloroform, toluene, benzene, diethylene glycol diethyl ether or the like. Alternatively, an organic solvent sparingly soluble in water may be employed, for example n-butanol. A sample of fermentation medium may typically contain on a weight/volume basis 175 to 1000 meg/ml of crude antibiotic although in high-yielding fermentations, concentrations several times higher than the quoted upper limit may be obtained. The obtained solvent is evaporated to dryness in vacuo, the residue weighed and dissolved in dimethylformamide to give a solution having an estimated antibiotic 67-121 concentration of approximately 1000 meg/ml. An aliquot of this solution is then taken and diluted with 0.1 molar phosphate buffer of pH 8.0 to give a solution having an estimated antibiotic 67-121 concentration of approximately 3 meg/ml. The precise concentration of antibiotic 67-121 in the latter solution is then determined using a standard cylinder cup assay with Saccharomyces cervisiae ATCC 9763 as the test organism and employing as standard a pure sample of antibiotic 67-121 complex which is assigned a potency of 1000 meg/mg.

The Antibiotic 67-121 reference standard employed has a potency of 4000 meg/mg, expressed as candicidin, in the candicidin assay set forth in Title 21 of the Code of Federal Regulation, Section 148v.

Isolation and Purification of the Antibiotic Product

Following peak production, the polyene antibiotic product is isolated from the fermented medium using methods known per se for polyene antibiotics.

Thus, for example, a method using the following sequence of steps may be employed:

(a) acidify the whole broth to a pH of 2.5 to 4.0;
(b) filter off the mycelium from the acidified broth;
(c) extract the mycelium one or more times with a suitable water immiscible or sparingly miscible organic solvent;
(d) combine the organic solvent extracts and evaporate to a residue;
(e) triturate the residue with a non-polar organic solvent such as a saturated or unsaturated hydrocarbon or an alkyl ether, preferably diethyl ether;
(f) filter off the resulting suspension which represents the crude antibiotic 67-121 complex.

Alternatively, the polyene antibiotic may be isolated by acidifying the whole broth to a pH of 2.5 to 4.0, directly extracting the acidified broth with a suitable water immiscible or sparingly miscible organic solvent and then subjecting the combined extracts to steps (d) to (f) above.

In use, we have found that by the above specified methods a crude antibiotic 67-121 complex assaying in the previously described cylinder cup assay at 250 meg/mg. can be obtained.

Purification of the crude polyene antibiotic complex may be effected by methods known in the art, such as fractional crystallisation, sequential dissolution and reprecipitation, counter-current extraction techniques and the like.

Thus, a crude antibiotic 67-121 product assaying at 250 meg/mg. may be purified by dissolving this product in the lower phase of a chloroform:methanol:water mixture having a volume ratio of 2:2:1.

The resulting solution is filtered to remove insoluble material and the filtrate is then added to diethyl ether (10 volumes diethyl ether to 1 volume of filtrate) and the resulting yellow precipitate filtered off. The precipitate is then dissolved in an adequate amount of the upper phase of the aforementioned chloroform:methanol:water mixture, filtered and the filtrate allowed to stand in vacuo until sufficient solvent has evaporated to result in precipitation of the purified antibiotic complex. The precipitated purified, antibiotic complex is filtered off, washed with diethyl ether and then dried in vacuo. The purified antibiotic 67-121 complex obtained in this manner assays at 1000 meg/mg. as antibiotic 67-121 complex (or at 4000 meg/mg. in terms of candicidin).

Separation of the Antibiotic Components

Suitably the antibiotic 67-121 complex may be separated into its components by chromatographic methods, such as by column chromatography. Specifically in employing column chromatography silica gel may be employed as the column material and the lower phase of a chloroform:methanol:water mixture (2:2:1 parts by volume) as the eluant.

If desired, prior to the above chromatographic separation step, a partial separation may be effected by dissolving the 67-121 complex in the lower phase of a chloroform:methanol:water mixture (2:2:1 parts by volume) and then effecting partial precipitation of the dissolved material by addition of methanol.

Column chromatographic separation of the Antibiotic 67-121 complex has shown the complex to comprise four component antibiotics herein designated Antibiotics 67-121A, 67-121B, 67-121C and 67-121D, this designation following the order in which the antibiotics emerge from the column. Using silica gel plates and the above specified solvent system, the determined Rf values for the individual components were antibiotic 67-121A=0.17, 67-121B=0.14, 67-121C=0.11 and 67-121D=0.07. Elution of the antibiotic components from the column may be readily monitored on silica gel thin-layer plates using the solvent mixture employed in the column chromatographic separation, the presence of antibiotic material on the plate being identified by any convenient means such as by bioautography or alternatively by spraying the plate with say a sulfuric and methanol mixture and then heating the plate to reveal the presence of antibiotic material.

The relative proportion of the antibiotic components may well vary from one fermentation to another, but in general it may be said that Antibiotic 67-121C will usually be the major component and 67-121D a trace component.

By way of illustration, it may be mentioned that in a specific example the relative proportions of components on a weight basis were 67-121A 12%, 67-121B 12%, 67-121C 76% and 67-121D trace.

The Antibiotic Products

As previously stated the Antibiotic 67-121 complex comprises the component antibiotics designated 67-121A, 671-121B, 671-121C and 671-121D, and these antibiotics have been classified as polyene macrolide antibiotics. Further, from their characteristic ultraviolet absorption spectra and infrared absorption spectra, the antibiotics have been classified as heptaene macrolide antibiotics.

Chemical and physical data for the antibiotic 67-121 complex and its components are set forth below.

CHEMICAL AND PHYSICAL PROPERTIES OF ANTIBIOTIC 67-121 COMPLEX

Table 1 below sets forth ultraviolet absorption spectral data for a sample of Antibiotic 67-121 complex and, for comparison purposes, corresponding data taken from the literature for a number of other heptaene antibiotics. Table 2 correspondingly sets forth data for elemental analysis, optical rotation, melting point and also lists $R_f$ values. These $R_f$ values were obtained with a solvent system consisting of a mixture of n-butanol (6 parts), acetic acid (2 parts), water (2 parts) and dioxane (1 part) and detection was made either by bioautography against *Candida albicans* or by spraying the chromatographic plate with a sulfuric acid, methanol spray.

In Table 3 certain stability data for the Antibiotic 67-121 complex are presented, the antibiotic being heated with the appropriate 0.1 M buffer for the stated periods of time on a boiling water bath. Specifically, a borate buffer was employed for pH values 9.0 to 10.0 and for the range 2.2 to 8.0 buffers marketed under the trade designation McIlvaines buffer were employed. The stability was ascertained by determining the antifungal activity, after heating for the specified time, using a disc assay method (6.25 mm discs) with *Candida albicans* as the test organism. The results are expressed in terms of the diameter of the zone of inhibition given in mm. From Table 3 it will be seen that the Antibiotic 67-121 complex is fairly stable at 100° C. in the pH range of 7.0 to 9.0. At pH 10 it is somewhat less stable, the activity decreasing rapidly after 15 minutes at 100° C. Below pH 5.0 the antibiotic is relatively unstable.

As will be seen from Table 2, the Antibiotic 67-121 complex can be distinguished chromatographically from the other specified antibiotics with the exception of candidin. Antibiotic 67-121 can be distinguished from candidin, however, on the basis its elemental analysis and optical rotation (for the latter see the values given thereinafter for the components B, C and D).

To further characterise the Antibiotic 67-121 complex, a standard classification procedure for heptaene antibiotics was employed (see Tetrahedron 25 pp 2229-2232). Acid hydrolysis yielded an amino sugar moiety and, in addition, potassium hydroxide treatment yielded an aromatic ketone moiety, the antibiotic product being accordingly placed in the heptaene subgroup II classification. The heptaene subgroup II includes such known antibiotics as candicidin, trichomycin B and perimycin.

TABLE 1

Ultra violet absorption data
Maxima and in brackets $E_{1cm}^{1\%}$ values.

| Antibiotic | Maxima in mμ in MeOH | Maxima in mμ in EtOH |
| --- | --- | --- |
| Antibiotic 67-121 complex | 342(340), 363(475), 382(667), 403(605) | 344(385) 362(490), 382(690) 404(625) |
| Ascosin "A" | | 340, 358, 377, 399 |
| Ascosin "B" | | 340, 358, 376, 398 |
| Candicidin | | 360, 380, 403 |
| Candidin | 363(1000), 382(1650) 406(1860) | 364(985), 385(1730), 407(1910) |
| Candimycin | 362, 382, 406 | |
| Fungimycin | | 358, 376, 399 |
| Hamycin | 230, 285, 345, 363 383(962), 406(918) | |
| Trichomycin "A" | 361.5(625), 382(863) 404(750) | 286, 346, 364, 384, 405 (Trichomycin complex) |
| Trichomycin "D" | 358, 377, 400 | |

TABLE 2

| Antibiotic | Elemental Analysis C | H | N | Optical Rotation | M.P. °C. | $R_f$ |
| --- | --- | --- | --- | --- | --- | --- |
| Antibiotic 67-121 Complex | 56.14 | 7.53 | 1.79 | | 175 | 0.43 |
| Ascosin "A" plus Ascosin "B" | | | | +13°* | | 0.53 |
| Candicidin | 63.29 | 7.16 | 2.33 | | | 0.54 |
| Candidin | 60.06 | 9.65 | 1.65 | +363°** | 180 | 0.45 |
| Candimycin | 57.17 | 8.81 | 1.70 | | 230 | 0.53 |
| Fungimycin | | | | | | 0.54 |
| Hamycin | 59.5 | 8.3 | 2.2 | +216°*** | 160 (no definite m.p.) | 0.52 |
| Trichomycin "A" | 60.06 | 7.62 | 2.28 | | 320 (decomposition) | 0.55 |
| Trichomycin "B" | 59.49 | 8.09 | 2.16 | | | |

*in dimethylformamide; literature source does not specify concentration.
**0.3% in dimethylformamide
***0.1% in pyridine

TABLE 3

Heat and pH Stability of Antibiotic 67-121 complex
(Expressed in terms of Antifungal Activity)
Time of Exposure at 100° C.
Results expressed in terms diameter of zone of inhibition in mmm

| pH | 0 min. | 5 min. | 15 min. | 30 min. |
| --- | --- | --- | --- | --- |
| 2.2 | 0 | 0 | 0 | 0 |
| 3.0 | 0 | 0 | 0 | 0 |
| 4.0 | 12 | 9 | 0 | 0 |
| 5.0 | 14 | 14 | 13 | 11 |
| 6.0 | 15 | 15 | 15 | 11 |
| 7.0 | 15 | 14 | 14 | 14 |
| 8.0 | 17 | 16 | 15 | 13 |
| 9.0 | 17 | 16 | 13 | 12 |
| 10.0 | 16 | 15 | 11 | 0 |

Chemical and Physical Properties of the Antibiotic 67-121 Components

Antibiotic 67-121A

Colour and form - Yellow needles
m.p. = 185°-190° C. (Decomposition)
Elemental Analysis
C = 59.40%
H = 7.90%

-continued

Chemical and Physical Properties of the Antibiotic 67-121 Components

N = 2.60%
M. Wt. = 1218 (osmometry)
$[\alpha]_D^{26}$ = +161.6° (0.3% in dimethylformamide)
pka = 6.0 (COO⁻)
     9.0 (NH₃⁺) (66% aqueous dimethyl formamide)

U.V. data (in tetrahydrofuran: water, ratio 4:1)
  λ max  408 mμ ($E_{1cm}^{1\%}$ = 950)
         384 mμ ($E_{1cm}^{1\%}$ = 1100)
         363 mμ ($E_{1cm}^{1\%}$ = 680)

I.R. data (in Nujol)
  ν max  3350, 1725 and 1665 cm⁻¹

NMR data (in hexa-deutero-dimethylsulfoxide)
  δ    2.73 ppm (3H, singlet, aromatic-N—CH₃)
       6.55 ppm (2H, doublet, J = 8.5 Herz., aromatic H)
       7.64 ppm (2H, doublet, J = 8.5 Herz., aromatic H)

Antibiotic 67-121B

Colour and form - Yellow needles
m.p. = 175°–182° C. (Decomposition)
Elemental Analysis
  C = 59.70%
  H = 7.65%
  N = 2.17%
M. Wt. = 1218 (osmometry)
$[\alpha]_D^{26}$ = +199.7° (0.3% in dimethylformamide)
pka = 6.3 (COO⁻)
     9.0 (NH₃⁺) (66% aqueous dimethyl formamide)

U.V. data (in tetrahydrofuran: water, ratio 4:1)
  λ max  408 mμ ($E_{1cm}^{1\%}$ = 620)
         383 mμ ($E_{1cm}^{1\%}$ = 750)
         362 mμ ($E_{1cm}^{1\%}$ = 490)

I.R. data (in Nujol)
  ν max  3350, 1725 and 1665 cm⁻¹

NMR data (in hexa-deutero-dimethylsulfoxide)
  δ    6.58 ppm (2H, doublet, J = 8.5 Herz., aromatic H)
       7.60 ppm (2H, doublet, J = 8.5 Herz., aromatic H)

Antibiotic 67-121C

Colour and form - Yellow needles
m.p. = 175°–180° C. (Decomposition)
Elemental Analysis
  C = 57.06%
  H = 7.30%
  N = 2.07%
M. Wt. = 1266 (osmometry)

$[\alpha]_D^{26}$ = +143.8° (0.3% in dimethylformamide)
pka = 6.0 (COO⁻)
     9.0 (NH₃⁺) (66% in aqueous dimethylformamide)

U.V. data (in tetrahydrofuran: water, ratio 4:1)
  λ max  408 mμ ($E_{1cm}^{1\%}$ = 800)
         383 mμ ($E_{1cm}^{1\%}$ = 910)
         362 mμ ($E_{1cm}^{1\%}$ = 600)

I.R. data (in Nujol)
  ν max  3350, 1725 and 1665 cm⁻¹

NMR data (in hexa-deutero-dimethylsulfoxide)
  δ    2.76 ppm (3H, singlet, aromatic N—CH₃)
       6.57 ppm (2H, doublet, J = 8.5 Herz., aromatic H)
       7.65 ppm (2H, doublet, J = 8.5 Herz., aromatic H)

As for the antibiotic 67-121 complex, the individual component antibiotics from their characteristic ultraviolet and infra-red absorption spectra are classified as heptaene macrolide antibiotics having numerous hydroxyl groups attached to the macrolide ring. Further, the individual components are classified as heptaene subgroup II antibiotics (see the hereinbefore specified classification). Degradation studies, as well as nuclear magnetic resonance and mass spectrometric data, show that the individual components contain the aromatic ketonic moiety:

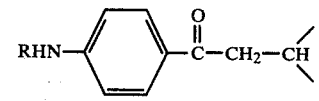

in which, for antibiotics 67-121 A and C, R is methyl and for Antibiotic 67-121 B, R is hydrogen.

Acetolysis of antibiotics 67-121A and 67-121B reveals the presence of a D-mycosamine sugar unit glycosidically attached to an allylic hydroxy group of the aglycone.

Acetolysis of antibiotic 67-121C reveals the presence of a novel disaccharide unit attached to an allylic hydroxy group of the aglycone, the disaccharide being indicated as [O-B-D-mannopyranosyl (1→4)-D-mycosamine] of the formula

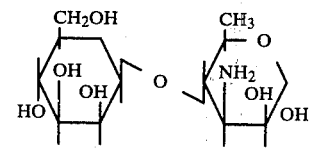

wherein the wavy line denotes that the stereochemistry of the glycosidic linkage of the disaccharide to the aglycone has not yet been established.

Antibiotic 67-121A and Antibiotic 67-121C have the following structural formulae:

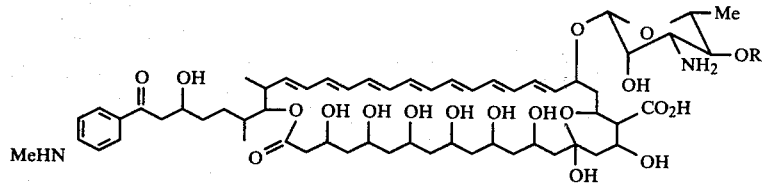

R = 1-O-β-D-Mannosyl
(67-121-C, $C_{65}H_{98}N_2O_{24}$)
R = H
(67-121-A, $C_{59}H_{88}N_2O_{19}$)

As can be seen by the formulae and by the physicochemical data set forth on pages 30–33, the antibiotic components contain a carboxylic acid group which is amenable to salt and ester formation by methods known per se. Thus, for example, we have obtained corresponding esters using a diazomethane route, these esters also being found to possess antifungal activity. The antibiotic and esters thereof form acid addition salts with the appropriate acids for example mineral acids such as hydrochloric acid, sulfuric acid and phosphoric acid or organic acids such as acetic acid, citric acid, tartaric acid and the like.

BIOLOGICAL ACTIVITY OF THE ANTIBIOTIC PRODUCTS

(A) In vitro antifungal activity

In vitro antifungal activity data for the antibiotic 67-121 complex are set forth in Table 4. For reference, data on candicidin are also given. The quoted minimal inhibitory concentrations (MIC) were obtained by conventional tube dilution techniques using Sabouraud's dextrose broth.

As representative of the component antibiotics, antibiotic 67-121A and antibiotic 67-121C were tested in the same manner as the complex. Antibiotic 67-121A gave MIC values of from less than 0.01 up to 0.03 meg/ml. against 18 strains of *Candida albicans*, while antibiotic 67-121C gave MIC values of 0.05 to 0.3 meg/ml. against 9 strains of *Candida albicans* after incubation times of 48 hours. Further testing of antibiotic 67-121C under the same conditions gave MIC values of 0.3 meg/ml. against two strains of Torulopsis and a single strain of Cryotococcus. Strains of Aspergillus and Dermatophytes were generally less sensitive with MIC values for antibiotic 67-121C of from 3 to 25 meg/ml.

TABLE 4

Antibiotic 67-121 complex - In vitro antifungal activity
Minimum Inhibitory Concentration (M.I.C.)
in meg/ml

| Organism | | 67-121 complex | | Candicidin | |
|---|---|---|---|---|---|
| | | 24 hrs. | 48 hrs. | 24 hrs. | 48 hrs. |
| *Candida albicans* | 406 | 0.03 | 0.3 | 0.03 | 0.08 |
| | 402 | 0.03 | 0.3 | 0.03 | 0.08 |
| | 420 | 3.0 | 3.0 | 3.0 | 7.5 |
| | 404 | 0.8 | 3.0 | 0.8 | 3.0 |
| | 403 | 0.03 | 0.3 | 0.03 | 0.08 |
| | 401 | 0.8 | 0.8 | 0.8 | 3.0 |
| | 1 | 0.3 | 0.3 | | |
| | 12031 | 0.3 | 0.3 | | |
| | Flo | 0.3 | 0.3 | | |
| | 404A | 0.3 | 0.8 | | |
| | 402A | 0.3 | 0.3 | | |
| *Terulopsis glabrata* | 1 | 0.3 | 0.8 | 0.03 | 0.3 |
| | 2 | 0.3 | 0.8 | 0.03 | 0.08 |
| | 3 | 0.3 | 0.8 | 0.03 | 0.08 |
| | 12 | 0.8 | 0.8 | | |
| | 16 | 0.3 | 0.8 | 0.03 | 0.3 |
| | 17 | 0.3 | 0.3 | 0.03 | 0.08 |
| | 24 | 0.8 | 0.8 | | |
| | 27 | 0.8 | 3.0 | | |
| | 34 | 0.3 | 0.3 | | |
| | 76 | 0.3 | 0.3 | | |
| | 46 | 0.3 | 0.3 | | |
| | | 72 hrs. | | | |
| *Aspergillus niger* | | 7.5 | | 7.5 | |
| *Trichophyton mentagrophytes* 17 | | 7.5 | | 25 | |
| *Trichophyton mentagrophytes* 1A | | 3.0 | | 17.5 | |
| *Trichophyton soudanese* 2 | | 7.5 | | 25 | |
| Trichophyton - 16 strains (12 species) | | 5.0 | | | |
| Microsporum - 6 strains (6 species) | | 5.0 | | | |
| *Microsporum distortum* | | 3.0 | | | |
| Phialophore (2 strains) | | 5.0 | | | |

(B) In Vivo Antifungal Activity

The in vivo protective activity of the antibiotic products in mice (Carworth farm CF 1 mice, each weighing about 20 g.) against *Candida albicans* was determined. The antibiotic was administered by the stated route in an aqueous vehicle containing 0.5% carboxymethyl cellulose and in two doses. One dose was administered shortly before intravenous infection with a lethal dose of *Candida albicans* and the other dose was administered 4 hours after infection. Most of the unprotected control mice died within 24 to 48 hours after infection. The survival rate was determined at the end of 24 and 48 hours and from this using standard procedures the $PD_{50}$ values were determined.

The results obtained for the Antibiotic 67-121 complex are given in Table 5 together with data for candicidin (for comparison purposes). The $PD_{50}$ values were determined on survivors 48 hours after infection.

TABLE 5

| | | $PD_{50}$ (mg/kg) | | Controls (% survivors) | |
|---|---|---|---|---|---|
| | | Antibiotic | | | |
| Test | Route | 67-121 complex | Candicidin | 24 hrs. | 48 hrs. |
| 1 | Subcutaneous | 2.5 | 5 | 20 | 20 |
| | Oral | 2.5 | 25 | | |
| 2 | Subcutaneous | 5.0 | 5 | 50 | 16 |
| | Oral | 2.5 | 5 | | |
| 3 | Subcutaneous | 15 | 25 | 0 | 0 |
| 4 | Subcutaneous | 1.5 | 2.5 | 20 | 20 |
| | Oral | 1.5 | 40 | | |

The $PD_{50}$ values for antibiotics 67-121A, 67-121B and 67-121C using CF 1 mice were determined using essentially the above described method, with the exception that the antibiotic was administered as a single dose one hour after infection with *Candida albicans*.

The $PD_{50}$ values were determined on survivors 72 hours after infection. Of the untreated, infected control mice, 80% died within 24 hours and 100% within 48 hours. The results are given in Table 6.

TABLE 6

| | In vivo antifungal activity | | |
|---|---|---|---|
| | $PD_{50}$ (mg/kg) | | |
| Route | Antibiotic 67-121A | Antibiotic 67-121B | Antibiotic 67-121C |
| Subcutaneous | 2.5 | 15.0 | 2.1 |
| Oral | 1.5 | 18.0 | 1.5 |

(C) Acute Toxicity Data

The acute toxicity of the antibiotic 67-121 complex in mice was determined via intraperitoneal (I.P.) and subcutaneous (S.C.) administration. For comparison, the values of candicidin were determined. The results are given in Table 7 below.

TABLE 7

| | $LD_{50}$ (mg/kg) | |
|---|---|---|
| Route | Antibiotic 67-121 complex | Candicidin |
| I.P. | 5-15 | 8-22 |
| S.C. | 300 | 300 |

Similarly, in another series of tests the acute toxicity of antibiotics 67-121A, 67-121B and 67121C were determined in male CF 1 mice. The results are given in Table 8 below.

TABLE 8

| Route | LD₅₀ (mg/kg) | | |
|---|---|---|---|
| | Antibiotic 67-121A | Antibiotic 67-121B | Antibiotic 67-121C |
| I.P. | 2.4 | 6.0 | 6.0 |
| S.C. | >50 | >50 | — |
| Oral | >50 | >50 | — |

The novel antibiotic products may typically be administered topically, orally or parentally, in free form or in the form of a suitable derivative, and preferably in admixture with a pharmaceutically acceptable carrier or excipient.

The precise dose to be administered in any particular dosage form will depend upon such factors as the stage and severity of the infection, the susceptibility of the infecting organism to the antibiotic and the individual characteristics of the animal species being treated. It may be said, however, that for intravenous use of the antibiotics of this invention an amount of from about 0.25 mg. to about 1.5 mg. per kilogram of body weight per dose is indicated. For oral administration, a dose in the range of 5 to 50 mgs. would be indicated. In the foregoing, the individual dose would be administered one to four times a day. Topical preparations would usually be administered in the form of creams, ointments, powders or vaginal suppositories. Oral preparations would be in the form of elixirs, tablets, capsules and the like.

EXAMPLES

The invention will now be further illustrated by way of the following examples in which Example 1 illustrates the cultivation of *Actinoplanes caeruleus* (specifically, that assigned NRRL 5325 was employed) and production of antibiotic 67-121 complex, Examples 2 to 5 illustrate the isolation and purification of the 67-121 complex, Example 6 illustrates the resolution of the 67-121 complex into its component antibiotics, Examples 7 and 8 illustrate the preparation of specified derivatives of antibiotic 67-121C and the remaining Examples illutrate compositions containing specified antibiotic products.

EXAMPLE 1

Cultivation of *Actinoplanes caeruleus* and Production of Antibiotic 67-121 complex.

A. Inoculum Preparation

Add a loopful (e.g. about 0.5 ml.) of culture from an agar slant of *Actinoplanes caeruleus* to each of a series of 300 ml. Erlenmeyer flasks containing 100 ml. of a sterile medium having the following composition:

| Beef extract | 3.0 g. |
|---|---|
| Yeast extract | 5.0 g. |
| Tryptose | 5.0 g. |
| Soluble starch | 24.0 g. |
| Dextrose | 1.0 g. |
| Calcium carbonate | 2.0 g. |
| Tap water | 1000 ml. |

Incubate the contents of the flasks with agitation on a rotary shaker at 250 to 300 rpm for about 48 hours at about 35° C.

B. Cultivation and Antibiotic Production

Transfer under aseptic conditions 5 ml. of the inoculum prepared in step A to each of a series of 500 ml. Erlenmeyer flasks containing 100 ml. of sterile medium having the following composition:

| Soybean meal | 30 g. |
|---|---|
| Dextrose | 40 g. |
| Calcium carbonate | 10 g. |
| Tap water | 1000 ml. |

Effect the submerged aerobic cultivation by fermenting the contents of the flasks at about 28° C. for 3 to 4 days with rotary agitation at about 300 rpm.

After about the first 24 hours, samples are periodically taken from the fermented media and assayed for antibiotic activity so that peak production, that is the stage at which the antibiotic activity of the fermented media reaches a peak can be ascertained. When fermentation is effectively complete, as evidenced by peak production, the contents of the flasks may be conveniently combined for subsequent isolation of the antibiotically active product.

Alternatively, the above fermentation may be carried out using other suitable media such as the following:

| (a) | Yeast extract | 5 g. |
|---|---|---|
| | Casein hydrolysate | 5 g. |
| | Dextrose | 10 g. |
| | Soluble starch | 20 g. |
| | Calcium carbonate | 4 g. |
| | Tap water | 1000 ml. |
| (b) | Soyabean meal | 30 g. |
| | Corn steep dried solids | 5 g. |
| | Starch | 20 g. |
| | Dextrose | 10 g. |
| | Calcium carbonate | 7 g. |
| | Tap water | 1000 ml. |

EXAMPLE 2

Isolation of the Antibiotic 67-121 Complex

Acidify the fermented medium obtained from Example 1 with a mineral acid such as hydrochloric acid to a pH of from 2.5 to 4.0. Add a suitable filter aid (we specifically employed that sold under the trade designation Hyflo-supercel which is a free flowing diatomaceous earth marketed by Johns Manville Co. U.S.A.) and then extract the resulting filter cake repeatedly with n-butanol until the filter cake is substantially free of antibiotic material. Combine the n-butanol extracts and evaporate in vacuo to a residue. Triturate the residue with a mixture containing by volume 1 part of diethyl ether to 1 part of acetone, filter, re-triturate the residue with diethyl ether, again filter and then dry the resulting residue in vacuo. The resulting antibiotic-121 complex is generally a green-yellow powder assaying in the hereinbefore specified cylinder cup assay at 1000 mcg/mg. as candicidin or 250 mcg/mg. as antibiotic 67-121 complex.

EXAMPLE 3

Alternative Isolation Method for the Antibiotic 67-121 Complex

Treat the fermented medium as described in Example 2 to give a filter cake and then wash this cake with acetone to remove most of the water. Extract the filter cake with a mixture consisting of both phases of a chloroform:methanol:water mixture having a volume/volume ratio of 18:6:1 until the filter cake is substantially free of antibiotic. Combine the extracts, separate the liquid phases, discard the aqueous phase and then evaporate the organic phase to a residue of crude antibiotic 67-121 complex assaying at about 250 mcg/mg.

EXAMPLE 4

Further Isolation Method for the Antibiotic 67-121 Complex

Acidify one liter of the fermentation broth obtained from Example 1 with a mineral acid such as hydrochloric acid to a pH of about 3.5. Extract the acidified broth twice with two liter portions of butanol saturated with water.

Evaporate the combined extracts to a residue and then dissolve the residue in the lower phase of a chloroform:methanol:water mixture having a volume ratio of 2:2:1. Dry the solution over anhydrous sodium sulfate and filter. Pour the dried solution into a diethyl ether:-hexane mixture having a volume ratio of 6:4 while vigorously agitating the mixture. Filter and dry the resulting yellow-brown precipitate of crude antibiotic 67-121 complex (assaying at about 250 mcg/mg.). We have obtained a yield of 940 mg. of product.

EXAMPLE 5

Purification of the Antibiotic Complex

Dissolve 3.9 g (obtained as described in Example 2) in the lower phase of a chloroform:methanol:water mixture (2:2:1). Filter off the insolubles and then add the filtrate to anhydrous diethyl ether. Filter the resulting yellow precipitate, wash several times with diethyl ethyl, and redissolve in the upper phase of the same system. Filter off the insolubles under vacuum. During the filtration a precipitate will form in the filtrate which is then filtered off, washed 3 to 4 times with diethyl ether and dried under vacuum. A yield of 410 mg. is obtained, the material having a potency of about 1000 mcg/mg as antibiotic 67-121.

EXAMPLE 6

Separation of the Antibiotic Complex into its Components

To a 5 cm. diameter column and 800 g. of chromatographic silica gel then, using as an eluant the lower phase of a freshly prepared mixture of chloroform:methanol:-water (2:2:1 ratio by volume), elute 4.6 g. of the antibiotic 67-121 complex obtained as for example by the method of Example 3.

Monitor the emergence of the antibiotic components by sampling the fractions collected and subjecting the samples to thin-layer chromatography or other suitable technique. Combine the eluate fractions containing each antibiotic fraction and concentrate to give the individual antibiotic fractions.

The following results were obtained:

| Antibiotic component | $R_f$ | Weight | m.p. °C. | $[\alpha]_D^{26}$ (0.3% dimethyl formamide) |
|---|---|---|---|---|
| 67-121A | 0.17 | 0.262g. | 185–190* | +161.6 |
| 67-121B | 0.14 | 0.260g. | 175–182* | +199.7 |
| 67-121C | 0.11 | 1.640g. | 175–180* | +143.8 |

-continued

| Antibiotic component | $R_f$ | Weight | m.p. °C. | $[\alpha]_D^{26}$ (0.3% dimethyl formamide) |
|---|---|---|---|---|
| 67-121D | 0.07 | trace | — | — |

(*decomposition)

EXAMPLE 7

Preparation of Antibiotic 67-121C Methyl Ester

Dissolve 5 g. of antibiotic 67-121C in 150 ml. of dimethyl sulphoxide and 15 ml. of methanol. Cool the solution to about 5° C. and add 0.5 g. of diazomethane in 30 ml. of tetrahydrofuran. Allow the reaction to continue for 10 minutes then pour the solution into 10 volumes of vigorously agitated diethyl ether. Collect the product by filtration or centrifugation and wash with fresh diethyl ether. Dissolve the precipitate in the lower phase of a chloroform, methanol, water mixture (2:2:1 v/v), chromatograph on 500 g. of silica gel using the same solvent mixture, and obtain thereby 1.1 g of the title compound, having the following characteristics:

m.p. = 180°–183° C.;
elemental analysis: C=56.30%, H=7.21%, N=1.84%.
λmax. (in tetrahydrofuran, water mixture 4:1 parts by volume) 409 mμ ($E_1\ _{cm}^{1\%}=650$), 385 mμ ($E_1\ _{cm}^{1\%}=770$), 364 mμ ($E_1\ _{cm}^{1\%}=515$);
δ(hexa-deutero-dimethyl sulfoxide) 3.4 ppm (3H, singlet, COOCH$_3$).

By substituting an equivalent quantity of antibiotic 67-121A or antibiotic 67-121B for antibiotic 67-121C in the foregoing example and by following the procedure of said example, the methyl esters of the respective antibiotics may be prepared.

Similarly, other esterifying agents may be employed to form other lower alkyl esters such as ethyl, propyl, isopropyl, butyl or the like.

EXAMPLE 8

Preparation of Antibiotic 67-121C Methyl Ester Hydrochloride

Dissolve 1.3 g. of Antibiotic 67-121C methyl ester (prepared as described in Example 7) in a mixture of tetrahydrofuran and water (4:1 v/v) and cool to about 10° C. Add 10 ml. of 0.1 N hydrochloric acid to the solution, concentrate to a residue, redissolve in water and lyophilize to obtain 1.1 g. of Antibiotic 67-121C methyl ester hydrochloride having the following characteristics:

m.p. = 170°–180° C. (decomposition),
λmax. (in tetrahydrofuran, water mixture, 4:1 parts by volume); 408 mμ ($E_1\ _{cm}^{1\%}=750$); 384 mμ ($E_1\ _{cm}^{1\%}=970$), 363 ($E_1\ _{cm}^{1\%}=580$). The % chlorine found was 2.20% weight/weight.

By replacing the hydrochloric acid in the foregoing example with an equivalent quantity of other pharmaceutically acceptable acids, preferably mineral acids, other acid addition salts may be prepared. Exemplary of such acids are sulfuric, phosphoric, nitric, hydrobromic, acetic propionic, isobutyric, maleic, oxalic, phenylacetic, methanesulfonic or the like.

The following Examples exemplify some of the dosage forms in which the antibiotic products of this invention and their derivatives may be employed:

EXAMPLE 9

| Ingredient | Tablets 5 mg. * Tab. | 50 mg. * Tab. |
|---|---|---|
| Antibiotic 67-121 complex | 5.00 mg. | 50.00 mg. |
| Lactose, U.S.P. | 164.25 mg. | 114.25 mg. |
| Corn starch | 50.00 mg. | 50.00 mg. |
| Polyvinylpyrrolidone | 12.50 mg. | 12.50 mg. |
| Magnesium stearate | 1.25 mg. | 1.25 mg. |
| Water q.s. (evaporates) | | |

Procedure

Prepare a slurry consisting of the Antibiotic 67-121 complex, lactose, water and polyvinylpyrrolidone. Spray dry the slurry. Add the corn starch and magnesium stearate. Mix and compress into tablets.

EXAMPLE 10

| Capsule | |
|---|---|
| Antibiotic 67-121C | 5.00 mg. |
| Lactose U.S.P. | 180.75 mg. |
| Magnesium stearate | 1.25 mg. |
| Corn starch | 46.00 mg. |
| Sodium lauryl sulfate | 12.00 mg. |
| | 245.00 mg. |

Procedure:
1. Blend the Antibiotic 67-121C and the lactose.
2. Add the magnesium stearate sodium lauryl sulfate, and corn starch, and mix.
3. Fill capsule.

EXAMPLE 11

| Oral Suspension (to give a dose of 25 mg/5 ml.) | |
|---|---|
| Antibiotic 67-121C tartrate | 5.00 g. |
| Magnesium Aluminum Silicate | 9.5 g. |
| Sodium Carboxymethylcellulose, U.S.P. | 2.5 g. |
| Sodium Citrate, U.S.P. | 25.0 g. |
| Flavor | q.s. |
| Color | q.s. |
| Methylparaben, U.S.P. | 0.9 g. |
| Propylparaben, U.S.P. | 0.2 g. |
| Polysorbate 80, U.S.P. | 1.0 g. |
| Sorbitol Solution, U.S.P. | 500.0 g. |
| Water q.s. | 1000.0 g. |

Procedure:
1. Heat 200 ml. of water to boiling, and dissolve in it one half of the parabens. Cool to about 70° C., then mix in the Polysorbate 80. Sprinkle in the silicate, stirring until a uniform smooth suspension results.
2. Heat an additional 200 ml. of water to boiling, and dissolve in it the remainder of the parabens. Disperse the carboxymethylcellulose in this until a smooth gel results. Mix in the Sorbitol Solution. Then introduce and dissolve the sodium citrate.
3. Add 2 to 1 slowly, with constant stirring. Cool

| Oral Suspension (to give a dose of 25 mg/5 ml.) |
|---|
| the mixture to 25° C. Add the antibiotic 67-121C, flavor and color, mixing thoroughly. Add sufficient quantity of water to make the total volume 1000 ml. |

EXAMPLE 12

| Topical Ointment | |
|---|---|
| Antibiotic 67-121C methyl ester | 10 g. |
| Petrolatum | 990 g. |
| | 1000 g. |

Procedure:
1. Melt the petrolatum.
2. Slurry the antibiotic 67-121C with about 10% of the petrolatum and pass through a colloid mill.
3. Mix the milled slurry with the remainder of the molten petrolatum. Allow to cool.

We claim:

1. A method of eliciting an antifungal response which comprises administering to an animal having a susceptible fungal infection an antifungal effective dose of the Antibiotic 67-121 Complex, a component thereof, a $C_1$–$C_4$ alkyl ester thereof having the formula

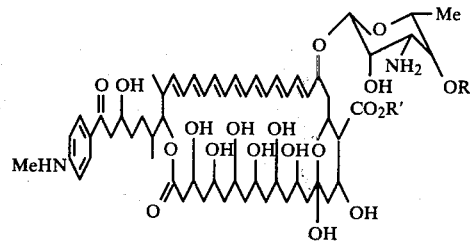

wherein R is hydrogen or 1-O-B-D-mannosyl, $R^1$ is hydrogen or $C_1$–$C_4$ lower alkyl, and the non-toxic pharmaceutically acceptable acid addition salts thereof.

2. A method according to claim 1 wherein a component of the Antibiotic 67-121 complex is administered.

3. A method according to claim 1 wherein a non-toxic pharmaceutically acceptable acid addition salt of a component of the Antibiotic 67-121 complex is administered.

4. A method according to claim 1 wherein an alkyl ester of a component of the Antibiotic 67-121 complex is administered.

5. The method of eliciting an antifungal response as defined in claim 1 wherein the dose of Antibiotic 67-121 complex administered intraveneously is from about 0.25 mg to about 1.5 mg per kilogram of body weight per dose.

6. The method of eliciting an antifungal response as defined in claim 1 wherein the dose of Antibiotic 67-121 complex administered orally is from about 5 mg to about 50 mg per kilogram of body weight per dose.

* * * * *